US009041851B2

(12) United States Patent
Forrest

(10) Patent No.: US 9,041,851 B2
(45) Date of Patent: May 26, 2015

(54) ORGANIC ELECTRONIC DETECTORS AND METHODS OF FABRICATION

(75) Inventor: Stephen Forrest, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 1217 days.

(21) Appl. No.: 11/272,796

(22) Filed: Nov. 15, 2005

(65) Prior Publication Data
US 2007/0108890 A1    May 17, 2007

(51) Int. Cl.
*H04N 5/232* (2006.01)
*H01L 27/146* (2006.01)
*H01L 27/30* (2006.01)
*H04N 5/369* (2011.01)
*H04N 5/225* (2006.01)

(52) U.S. Cl.
CPC ........ *H01L 27/14625* (2013.01); *H04N 5/2252* (2013.01); *H01L 27/146* (2013.01); *H01L 27/307* (2013.01); *H04N 5/225* (2013.01); *H04N 5/2254* (2013.01); *H04N 5/3696* (2013.01)

(58) Field of Classification Search
CPC .............. H01L 27/307; H01L 51/0002; H01L 51/0032; H04N 5/2252; H04N 5/2253
USPC ........................................................ 348/345
See application file for complete search history.

(56) References Cited

U.S. PATENT DOCUMENTS

| 4,444,471 | A | * | 4/1984 | Ford et al. | 359/676 |
|---|---|---|---|---|---|
| 4,467,361 | A | * | 8/1984 | Ohno et al. | 348/340 |
| 5,510,273 | A | * | 4/1996 | Quinn | 156/160 |
| 5,809,161 | A | * | 9/1998 | Auty et al. | 382/104 |
| 6,285,400 | B1 | * | 9/2001 | Hokari | 348/374 |
| 6,303,943 | B1 | | 10/2001 | Yu et al. | |
| 6,445,767 | B1 | * | 9/2002 | Karellas | 378/98.8 |
| 6,486,917 | B2 | * | 11/2002 | Iwasaki | 348/375 |
| 6,489,992 | B2 | * | 12/2002 | Savoye | 348/340 |
| 6,791,072 | B1 | * | 9/2004 | Prabhu | 250/208.1 |
| 6,836,135 | B2 | * | 12/2004 | Harris et al. | 324/765 |

(Continued)

FOREIGN PATENT DOCUMENTS

| JP | 01-202989 | 8/1989 |
|---|---|---|
| JP | 10062609 | 3/1998 |

(Continued)

OTHER PUBLICATIONS

Sun Yiru et al., "Direct patterning of organic light-emitting devices by organic-vapor jet printing", Applied Physics Letters, AIP, American Institute of Physics, Melville, NY, USA, vol. 86, No. 11, Mar. 8, 2005.*

(Continued)

*Primary Examiner* — Usman Khan
(74) *Attorney, Agent, or Firm* — Morgan, Lewis & Bockius, LLP

(57) ABSTRACT

The present invention is directed to a an organic imaging device having organic detectors on a curved surface. The device may be used for imaging applications such as photography, lightweight camera systems, very high-resolution imaging, lightweight "night vision", robotic vision, and others. A concave housing with a deformable lens is provided. The deformable lens allows for a range of fields of view and focal lengths. The invention may be configured to detect a range of electromagnetic radiation. It may then provide input to a computer, display, or other device for processing or display of the detected radiation as an image.

29 Claims, 5 Drawing Sheets

(56) References Cited

U.S. PATENT DOCUMENTS

| | | | |
|---|---|---|---|
| 6,985,184 B2* | 1/2006 | Sato | 348/340 |
| 7,009,647 B1* | 3/2006 | Kozlowski et al. | 348/294 |
| 7,072,120 B2* | 7/2006 | Lan | 359/664 |
| 7,359,124 B1* | 4/2008 | Fang et al. | 359/666 |
| 7,397,066 B2* | 7/2008 | Oliver | 257/81 |
| 7,399,274 B1* | 7/2008 | Halla et al. | 600/160 |
| 2001/0017651 A1* | 8/2001 | Baker et al. | 348/169 |
| 2001/0020671 A1* | 9/2001 | Ansorge et al. | 250/208.1 |
| 2002/0017612 A1* | 2/2002 | Yu et al. | 250/370.11 |
| 2003/0087471 A1* | 5/2003 | Shtein et al. | 438/82 |
| 2004/0085598 A1* | 5/2004 | Kokeguchi et al. | 358/909.1 |
| 2004/0101008 A1* | 5/2004 | Kurtz et al. | 372/39 |
| 2005/0030408 A1 | 2/2005 | Ito et al. | |
| 2005/0109918 A1* | 5/2005 | Nikzad et al. | 250/208.1 |
| 2005/0254133 A1* | 11/2005 | Akram et al. | 359/626 |
| 2008/0144185 A1* | 6/2008 | Wang et al. | 359/665 |

FOREIGN PATENT DOCUMENTS

| | | |
|---|---|---|
| JP | 2001-313410 | 11/2001 |
| JP | 2003-188366 | 7/2003 |
| JP | 2005 136325 | 5/2005 |
| JP | 2005 260436 | 9/2005 |
| JP | 2005-278133 | 10/2005 |
| WO | WO 97/26039 | 7/1997 |
| WO | WO 99/39372 | 8/1999 |
| WO | WO 03/067677 | 8/2003 |
| WO | WO 2004/006350 | 1/2004 |
| WO | WO 2004/072689 | 8/2004 |

OTHER PUBLICATIONS

European Patent Office, Search Report and Written Opinion for application PCT/US2006/040283, Oct. 29, 2007.

European Patent Office, Examination Report for application EP 06 825 982.9, Nov. 25, 2008.

Wang et al., "Auto-tunable microlens chip for sensing applications", Sensors, 2005 IEEE Oct. 31, 2005.

Saito et al., "Compound eye shaped flexible organic image sensor with a tunable visual field", Micro Electro Mechanical Systems, 2005, MEMS 2005. 18$^{th}$ IEEE International Conference, Jan. 30, 2005.

Kaneko et al., "A new smart vision system using a quick response dynamic focusing lens", The 13$^{th}$ Annual International Conference on Micro Electro Mechanical Systems, 2000, MEMS 2000, Jan. 23, 2000.

Mollers et al., "Improved light out-coupling in organic light emitting diodes employing ordered microlens arrayes", Journal of Applied Physics, American Institute of Physics, NY, USA, vol. 91, No. 5, Mar. 1, 2002.

Office Action in JP Application No. 2008-540032 dated Oct. 25, 2011.

Office Action in JP Application No. 2008-540032 dated Jun. 19, 2012.

* cited by examiner

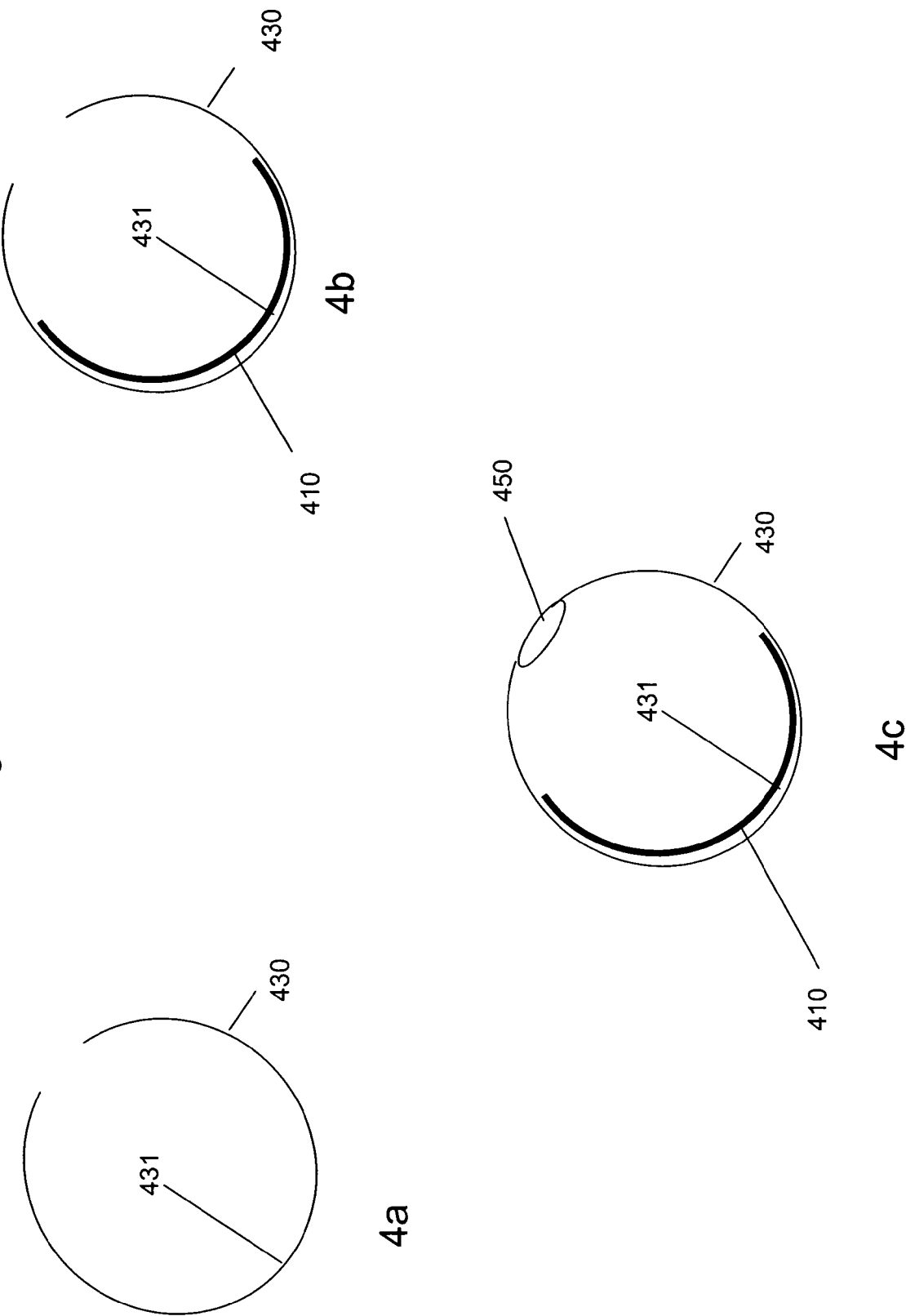

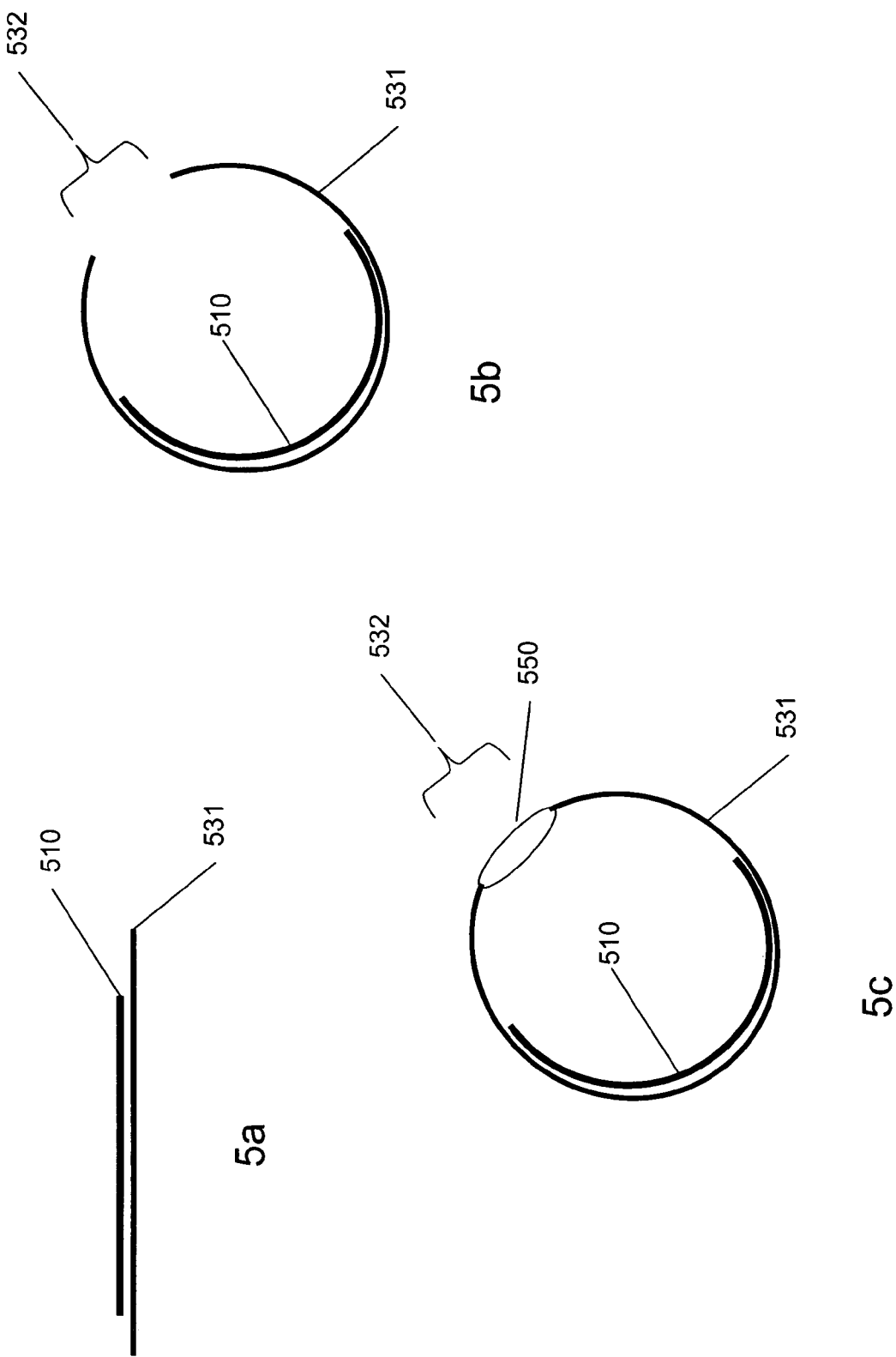

ORGANIC ELECTRONIC DETECTORS AND METHODS OF FABRICATION

GOVERNMENT RIGHTS

This invention was made with Government support under the U.S. Army Research Development and Engineering Award, Contract No. W911NF-04-1-0414 awarded by the Defense Advanced Research Projects Agency. The Government has certain rights in this invention.

JOINT RESEARCH AGREEMENT

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

BACKGROUND

Imaging devices, such as cameras, image sensors, and motion capture devices, are restricted in the field of view and depth of field available when compared to the human eye. Previous work has attempted to reproduce the variability of the human eye by, for example, approximating the curved surface of the retina with arrays of traditional imaging devices such as cameras and light sensors arranged on curved surfaces. Such attempts are limited in their use and construction, due to device complexity, limited resolution and fields of view, expense, generally high signal to noise density, and need for multiple lens systems. There is therefore a need for an imaging device that provides a simple imaging system that is lightweight, inexpensive, smaller, and that provides a large field of view without distortion.

The past fifteen years have seen an explosive growth of research interest in the study and application of organic materials as the active media in organic opto-electronic devices. Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate.

Examples of organic opto-electronic devices include organic light emitting devices (OLEDs), organic phototransistors, organic photovoltaic cells, organic photodetectors and other organic photosensitive devices.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. Similarly, photosensitive devices may generate voltage from incident light, and can therefore be used as detectors and, for example, in imaging devices such as cameras. Several opto-electronic materials and configurations are described in U.S. Pat. Nos. 5,844,363, 6,303,238, and 5,707,745, which are incorporated herein by reference in their entirety. Organic photosensitive devices are specifically described in U.S. Pat. No. 6,657,378, 6,451,415, which is incorporated herein by reference in its entirety.

Opto-electronic devices are generally (but not always) intended to emit or absorb light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit or absorb light only through the bottom electrode, the top electrode does not need to be transparent, and may be comprised of a thick and reflective metal layer having a high electrical conductivity. Similarly, for a device intended to emit or absorb light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

BRIEF DESCRIPTION OF THE DRAWINGS

FIG. 4 shows a method for fabricating a device in accordance with embodiments of the invention.

FIG. 5 shows another method for fabricating a device in accordance with embodiments of the invention.

DETAILED DESCRIPTION

The present invention is directed to a an organic imaging device having organic detectors on a curved surface. The device may be used for imaging applications such as photography, lightweight camera systems, very high-resolution imaging, lightweight "night vision", robotic vision, and others. A concave housing with a deformable lens is provided. The deformable lens allows for a range of fields of view and focal lengths. The invention may be configured to detect a range of electromagnetic radiation. It may then provide input to a computer, display, or other device for processing or display of the detected radiation as an image.

Figure 1:
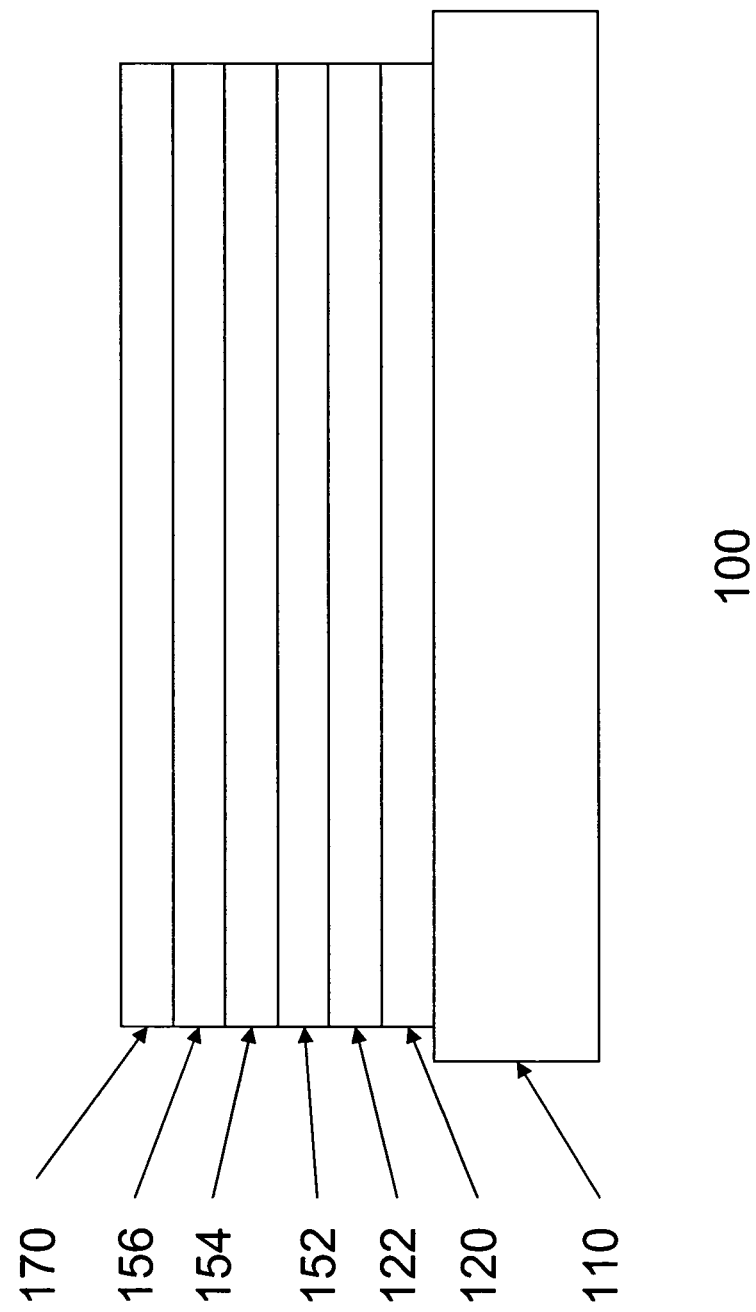
FIG. 1 is an example of an organic photosensitive device.

An organic photosensitive device comprises at least one photoactive region in which light is absorbed to form an exciton, which may subsequently dissociate into an electron and a hole. FIG. 1 shows an example of an organic photosensitive optoelectronic device 100 in which the photoactive region 150 comprises a donor-acceptor heterojunction. The "photoactive region" is a portion of a photosensitive device that absorbs electromagnetic radiation to generate excitons that may dissociate in order to generate an electrical current. Device 100 comprises an anode 120, an anode smoothing layer 122, a donor 152, an acceptor 154, an exciton blocking layer ("EBL") 156, and a cathode 170, over a substrate 110. As will be appreciated by one skilled in the art, other configurations are possible in organic photosensitive devices, which may include other or different layers.

Anode 120 and cathode 170 may be composed of metals or "metal substitutes." Herein the term "metal" is used to embrace both materials composed of an elementally pure metal, and also metal alloys which are materials composed of two or more elementally pure metals. The term "metal substitute" refers to a material that is not a metal within the normal definition, but which has the metal-like properties such as conductivity, such as doped wide-bandgap semiconductors, degenerate semiconductors, conducting oxides, and conductive polymers. Electrodes may comprise a single layer or multiple layers (a "compound" electrode), may be transparent, semi-transparent, or opaque. As used herein, a layer is said to be "transparent" if it transmits at least 50% of the ambient electromagnetic radiation in a relevant wavelength. As will be understood by one skilled in the art, other types and configurations of electrodes may be used.

The substrate 110 may be any suitable substrate that provides desired structural properties. The substrate may be flexible or rigid, planar or non-planar. The substrate may be transparent, translucent or opaque. Rigid plastics and glass are examples of preferred rigid substrate materials. Flexible plastics and metal foils are examples of preferred flexible substrate materials.

An anode-smoothing layer 122 may be situated between the anode layer 120 and the donor layer 152. Photoactive region 150 comprises donor material 152 and acceptor material 154. Organic materials for use in the photoactive region may include organometallic compounds, including cyclometallated organometallic compounds. Organic layers may be fabricated using vacuum deposition, spin coating, organic vapor-phase deposition, inkjet printing and other methods known in the art.

Figure 2:
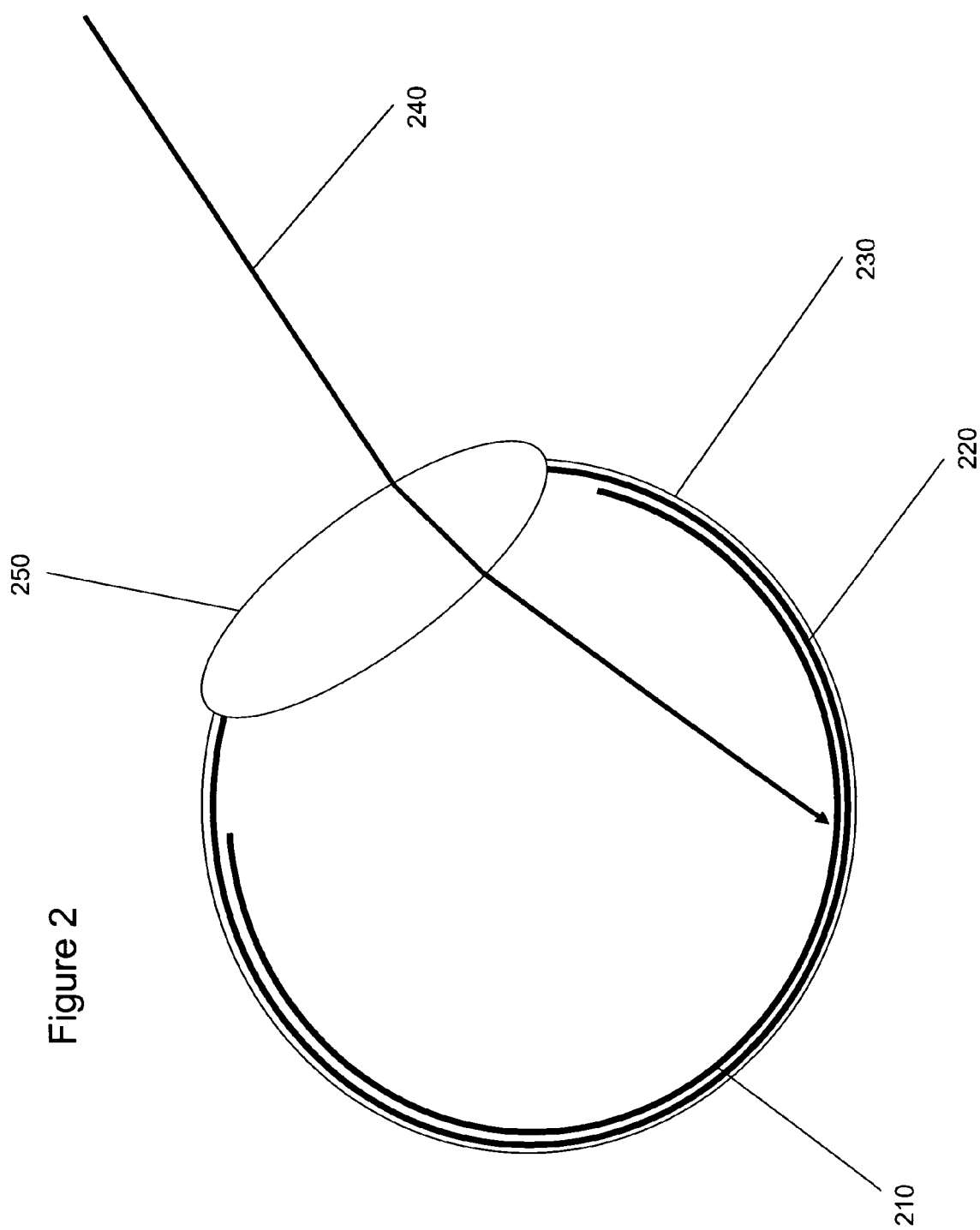
FIG. 2-3 show embodiments of the present invention.

FIG. 2 is an illustration of the present invention. Lens 250 has a curved focal plane in the shape of curved surface 230. Lens 250 may comprise a transparent elastomer, such as poly(dimethylsiloxane) (PDMS); other materials may be advantageous in certain configurations. Curved surface 230 may be spherical, roughly spherical, or ellipsoidal. Other shapes may also be desirable. Lens 250 is disposed in an opening in curved surface 230. The focal plane of lens 250 may be chosen to select for certain wavelengths of electromagnetic radiation 240 incident on the lens. Detector 210 is disposed on curved surface 230, such that incident electromagnetic radiation 240 transmitted through lens 250 will be detected. As will be understood by one skilled in the art, electromagnetic radiation 240 may comprise signals in the optical range, i.e., visible light. It may comprise signals with longer or shorter wavelengths, such as infrared, ultraviolet, or other wavelength ranges. In some embodiments, detector 210 comprises a plurality of organic photosensitive devices. Detector 210 may provide input to a data processing system (not shown). Detector 210 may be connected to backplane 220 to allow detector 210 to be used in an active matrix configuration. Backplane 220 may comprise thin film transistors.

Figure 3:
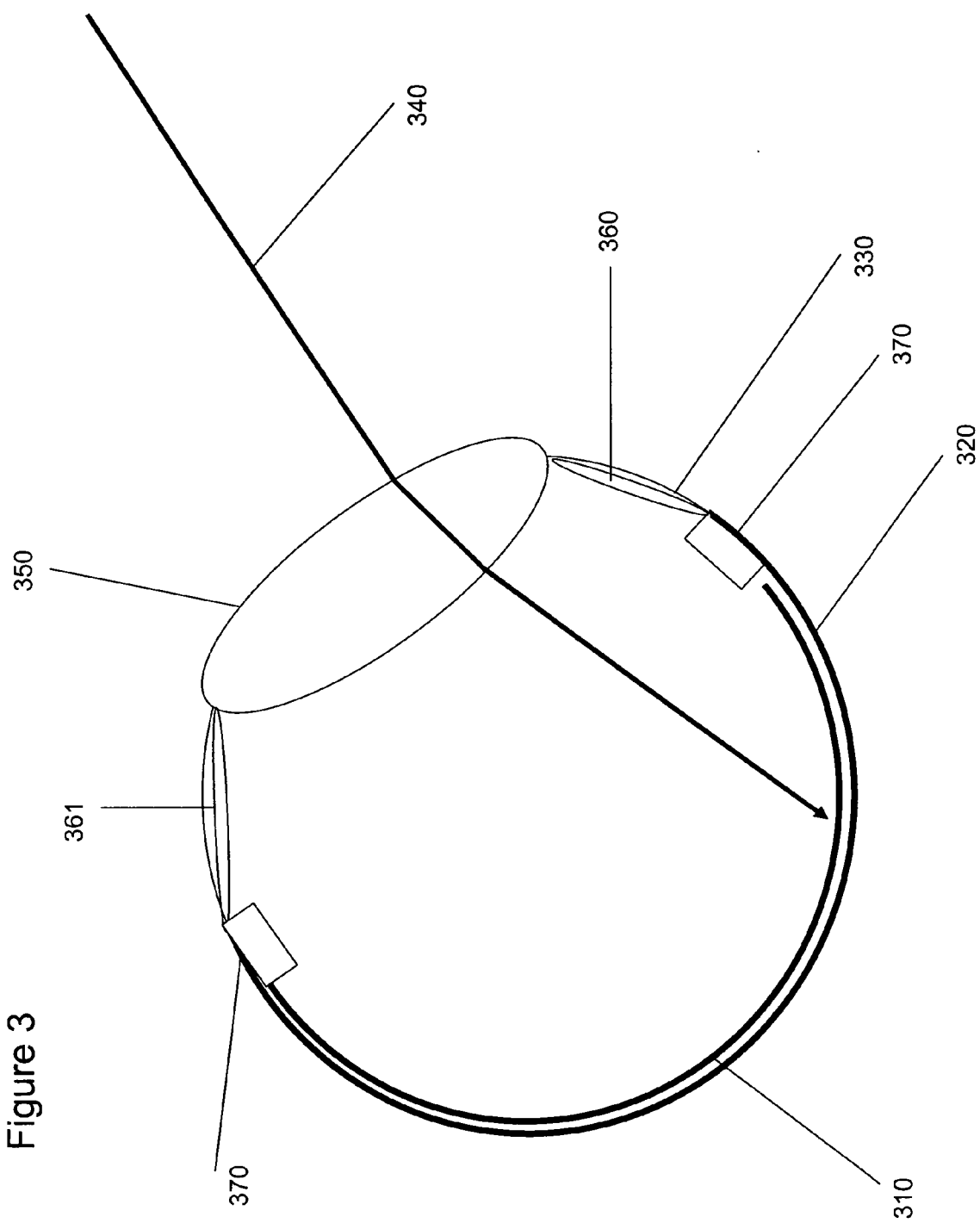

FIG. 3 is another illustration of the present invention. Deformable lens 350 is a deformable lens with a curved focal plane, disposed in an opening in curved surface 330. Incident electromagnetic radiation 340 is transmitted through deformable lens 350 and absorbed by organic detector 310. Depending on the specific application for which the device is used, the radius of curvature of surface 330 may vary. For example, in applications requiring a small device the radius may be on the order of a millimeter, while devices used in a larger application may have radii in the tens of meters.

The invention may include synthetic "muscles" 360 and 361, which may be disposed adjacent to and in physical contact with lens 350. As used herein and as will be understood by one skilled in the art, a synthetic muscle is a device that can expand and contract in response to an external signal. In preferred embodiments, muscles 360 and 361 comprise a polymer. Suitable materials for fabrication of polymer muscles include PDMS.

Polymer muscles 360 and 361 may be controlled by a computer or other processing system (not shown). It may be preferred that polymer muscles 360 and 361 are controlled by focusing mechanism 370. Focusing mechanism 370 may be disposed within, or on the interior of, the curved surface. It may use a stereo-computed range to determine appropriate focusing distance. Polymer muscles 360 and 361 may be made to expand or contract, thereby changing the focal plane, aperture, or focal length of deformable lens 350. Organic detector 310 is disposed on the concave side of curved surface 330, and is in the shape of the focal plane of lens 350. Backplane 320 may comprise an array of thin-film transistors, control and processing elements, or other devices. In preferred embodiments, detector 310 may comprise a plurality of organic detectors such as bilayer CuPc/$C_{60}$ diodes, multiple heterojunction diodes, or polymeric diodes. Detector 310 may provide input to a computer (not shown) for data processing.

Detector 310 may comprise a plurality of organic photosensitive devices disposed in an array. As will be understood by one skilled in the art, devices are arranged in an array if they are disposed in a roughly grid-like arrangement. Such arrangement may be preferable to facilitate use of the output of detector 310 as, for example, input to a processing device, display, or other device.

Detector 310 may comprise an active matrix, which further comprises an array of organic transistors and an array of organic photosensitive devices. Such arrangement may be preferable where it is desired to access signals from many directions simultaneously. Similarly, detector 310 may comprise a passive matrix array, which may be simpler to fabricate than an active matrix array, but which may require multiple detectors to share signal lines. In preferred embodiments, the detector will comprise a high-resolution detector array. This may be preferable in uses where detailed, large, or precise imagery is desired.

In some embodiments of the present invention, it may be advantageous to choose materials and configurations for the organic detector which allow for detection of light in non-visible regions of the electromagnetic spectrum. In preferred embodiments, the detector will detect light in the ultraviolet or infrared regions. Such photosensitive devices are described, for example, in U.S. Pat. Nos. 6,352,777, 6,297,495, 6,278,055, 6,198,091, and 6,198,091, all of which are incorporated herein by reference.

In order to provide a high resolution, it is preferable for the organic detector to cover a large percentage of the surface area with photosensitive material or devices available for receiving electromagnetic radiation. A higher coverage allows the device to capture more incident radiation. Achieving coverage and high resolution simultaneously may be an issue because each separate pixel may be surrounded by an area unable to receive electromagnetic radiation and convert it into current. Organic devices may mitigate this issue and therefore may provide an increased resolution. It is especially preferable that the detector of the present invention have a coverage of at least about 70%. Such a coverage may be achieved with organic devices, for example as described in U.S. Patent Application No. 2004/0032205, which is incorporated by reference in its entirety.

The present invention may provide a focusing mechanism controlling polymer muscles allows for adjustment of the focal length of the deformable lens. Polymer muscles 360 and 361 may deform lens 350 in order to adjust the f-number of the device. It is preferred that the device provides a range of f-numbers to allow flexibility in focusing. As will be understood by one skilled in the art, an "f-number" refers to the ratio of the size of an opening to the focal length of the lens transmitting light through that opening. An f-number is usually written as f/X, with X representing the ratio of focal length to aperture diameter. Note that f/8 is considered a larger f-number than f/1. For example, an f-number of f/8 represents a focal length that is 8 times the aperture diameter. In general, a lower f-number represents an increased sensitivity to electromagnetic radiation. A lower f-number may also result in a decreased depth of focus. It is advantageous to provide a range of sensitivity and depth of focus. Deformable lens 350 is capable of providing different f-numbers based on the degree to which it is deformed. In preferred embodiments, the present invention may be capable of providing an f-number as small as f/1. As will be understood by one skilled in the art, a lens is capable of providing a specific f-number if the f-number can be attained by deforming the lens within its expected tolerances. That is, a deformable lens may be deformable to a maximum amount in several directions; the lens is capable of providing the range of f-numbers that result from the range of deformations to which the lens may be subjected. The f-number of a deformable lens may be adjusted by deforming the lens in order to change the effective size of the opening in which the lens is disposed, to change the focal length of the lens, or both.

A process for fabricating a device in accordance with an embodiment of the invention is shown in FIG. 4. First, housing 430 with a non-developable concave interior surface 431 (4a) is obtained. A plurality of organic photosensitive devices 410 is deposited through the opening of housing 430 and onto interior surface 431 (4b). Deformable lens 450 is then placed in the opening of housing 430 (4c). As used herein and as will be understood by one skilled in the art, "non-developable" refers to a surface that cannot be deformed into a flat sheet without tearing, shearing, shrinking, or stretching. For example, a cylindrical surface is developable, whereas a spherical surface is non-developable. Photosensitive devices 410 may be deposited using, for example, organic vapor jet printing and ink jet printing. Organic devices are preferred for deposition on non-developable surfaces because organic vapor jet printing, ink jet printing, and similar fabrication methods may not be practiced for non-organic devices. Deposition onto a non-developable surface may be preferred because many preferred focal planes may have non-developable shapes, and deposition onto a planar surface followed by deformation of the surface into the desired shape may place considerable strain on the device. The devices may further comprise an active matrix or a passive matrix. For example, a layer comprising thin-film transistors may be deposited as a, or onto, a backplane on the non-developable surface. Other elements may be added to the invention. For example, polymer muscles and focusing mechanisms may be inserted into housing 430. An example configuration including such elements is shown in FIG. 3.

Another method for fabricating a device in accordance with an embodiment of the invention is shown in FIG. 5. A plurality of photosensitive devices 510 is deposited onto surface 531 (5a). Surface 531 is then deformed into a curved surface having opening 532 (5b). Deformable lens 550 is placed into opening 532 (5c). Photosensitive devices 510 may be deposited by, for example, organic vapor jet printing or ink jet printing. Photosensitive devices 510 may further comprise an active or passive matrix. The fabrication process may include other steps. For example, prior to deforming surface 531 or inserting deformable lens 550, polymer muscles, focusing mechanisms, or backplanes may be placed in the device.

The process described with respect to FIG. 5 may either be limited to developable shapes for surface 531, or may require tearing, shearing, shrinking, or stretching of surface 531 to achieve a non-developable surface. Nevertheless, devices fabricated using the process described with respect to FIG. 5 may be suitable for some uses.

While the present invention is described with respect to particular examples and preferred configurations, it is understood that the present invention is not limited to these examples and embodiments. The present invention as claimed therefore includes variations from the particular examples and preferred embodiments described herein, as will be apparent to one of skill in the art.

What is claimed is:

1. A device, comprising:
    a housing having a non-developable concave interior surface;
    an opening in the housing;
    a deformable lens having a curved focal plane and an adjustable focal length, the deformable lens being disposed in the opening;
    at least one polymer muscle in contact with the deformable lens, wherein the at least one polymer muscle is configured to change the size of the opening in the housing and the focal length of the deformable lens by expanding and contracting the polymer muscle itself in response to an external signal; and
    an organic detector disposed on the non-developable concave interior surface, wherein the non-developable concave interior surface is in the shape of the focal plane, and the detector is in the shape of the focal plane,
    wherein the organic detector comprises a plurality of organic photosensitive devices and has a surface area that comprises the plurality of organic photosensitive devices and area surrounding the organic photosensitive devices, the organic photosensitive devices covering at least 70% of the surface area of the organic detector.

2. The device of claim 1, wherein the detector further comprises a plurality of organic photosensitive devices.

3. The device of claim 2, wherein the plurality of organic photosensitive devices are disposed in an array.

4. The device of claim 1, wherein the at least one polymer muscle deforms the lens via electrically-controlled self-expansion and self-contraction of the polymer muscle itself.

5. The device of claim 1, further comprising a computer-controlled focusing mechanism to control motion of the at least one polymer muscle.

6. The device of claim 1, wherein the detector further comprises an active matrix further comprising an array of organic transistors and an array of organic photosensitive devices.

7. The device of claim 1, wherein the detector further comprises a passive matrix array of organic photosensitive devices.

8. The device of claim 1, wherein the detector is a high-resolution detector array.

9. The device of claim 1, wherein the detector detects light in the ultraviolet region.

10. The device of claim 1, wherein the detector detects light in the infrared region.

11. The device of claim 1, wherein the detector provides input to a computer for data processing.

12. The device of claim 1, wherein the lens is capable of providing an f-number of at least about f/1.

13. The device of claim 5, wherein the focusing mechanism uses a stereocomputed range to determine the focusing distance.

14. A method of fabricating a device, comprising:
 obtaining a housing having an opening therein and a non-developable concave interior surface;
 depositing a plurality of organic photosensitive devices through the opening and onto the non-developable concave interior surface; and
 inserting a deformable lens into the opening; wherein the deformable lens is connected to the housing using at least one polymer muscle; wherein the at least one polymer muscle is configured to change the size of the opening;
 wherein, the plurality of organic photosensitive devices are each surrounded by an area unable to receive electromagnetic radiation, and wherein the organic photosensitive devices are deposited so as to cover at least 70% of a surface area that comprises the plurality of organic photosensitive devices and the area surrounding the organic photosensitive devices.

15. The method of claim 14, wherein the plurality of organic photosensitive devices are deposited using organic vapor jet printing.

16. The method of claim 14, wherein the plurality of organic photosensitive devices are deposited using ink jet printing.

17. The method of claim 14, wherein the plurality of organic photosensitive devices are an active matrix further comprising a plurality of organic transistors and a plurality of photosensitive devices.

18. The method of claim 14, wherein the plurality of organic photosensitive devices comprise a passive matrix array of organic devices.

19. A device, comprising:
 a housing having an opening therein and a non-developable concave interior surface;
 a deformable lens having an adjustable focal length disposed in the opening;
 an organic detector disposed on the non-developable concave interior surface, the organic detector being in a position to detect optical signals transmitted through the deformable lens;
 an electrically-controlled polymer muscle attached to the deformable lens; and
 a computer-controlled focusing mechanism configured to control motion of the polymer muscle, wherein the polymer muscle is configured to change the size of the opening and the focal length of the deformable lens by expanding and contracting itself based on an electrical signal from the focusing mechanism; and
 wherein the organic detector comprises a plurality of organic photosensitive devices and has a surface area that comprises the plurality of organic photosensitive devices and area surrounding the organic photosensitive devices, the organic photosensitive devices covering at least 70% of the surface area of the organic detector.

20. The device of claim 19, wherein the organic detector is deposited using organic vapor jet printing.

21. The device of claim 19, wherein the organic detector is deposited using ink jet printing.

22. The device of claim 19, wherein the organic detector comprises an active matrix further comprising an array of organic transistors and an array of organic photosensitive devices.

23. The device of claim 19, wherein the organic detector further comprises a passive matrix array of organic photosensitive devices.

24. The device of claim 19, wherein the organic detector comprises a high-resolution detector array.

25. The device of claim 19, wherein the organic detector comprises devices sensitive to light in the ultraviolet region.

26. The device of claim 19, wherein the organic detector comprises devices sensitive to light in the infrared region.

27. The device of claim 19, wherein the organic detector provides input to a computer to process the data.

28. The device of claim 1, wherein the organic detector is deposited through an opening of a housing having a surface comprising the non-developable surface, onto a convex portion of the non-developable surface.

29. The method of claim 14, further comprising disposing the at least one polymer muscle around the deformable lens, the at least one polymer muscle configured to adjust at least one of a focal plane, an aperture, or a focal length of deformable lens via electrically-controlled self-contraction and self-expansion of the at least one polymer muscle itself.

* * * * *